United States Patent
Ha et al.

(10) Patent No.: US 12,115,290 B2
(45) Date of Patent: Oct. 15, 2024

(54) ODOR CONTROL COMPOSITION AND CARPET HAVING A DURABLE ODOR CONTROL PROPERTY

(71) Applicant: Microban Products Company, Huntersville, NC (US)

(72) Inventors: Mai Le Phuong Ha, Cornelius, NC (US); Karen Terry Welch, Kannapolis, NC (US); Bruno Michael Mourao, Cornelius, NC (US); Gina Parise Sloan, Statesville, NC (US)

(73) Assignee: Microban Products Company, Huntersville, NC (US)

( * ) Notice: Subject to any disclaimer, the term of this patent is extended or adjusted under 35 U.S.C. 154(b) by 145 days.

(21) Appl. No.: 16/156,258

(22) Filed: Oct. 10, 2018

(65) Prior Publication Data

US 2019/0105420 A1 Apr. 11, 2019

Related U.S. Application Data

(60) Provisional application No. 62/570,786, filed on Oct. 11, 2017.

(51) Int. Cl.
| | | |
|---|---|---|
| *A61L 9/01* | (2006.01) | |
| *A61K 8/368* | (2006.01) | |
| *A61K 8/37* | (2006.01) | |
| *A61L 9/012* | (2006.01) | |
| *A61Q 15/00* | (2006.01) | |
| *B32B 27/00* | (2006.01) | |
| *C11D 3/20* | (2006.01) | |
| *C11D 3/34* | (2006.01) | |
| *D06N 7/00* | (2006.01) | |
| *C11D 3/00* | (2006.01) | |

(52) U.S. Cl.
CPC ............... *A61L 9/01* (2013.01); *A61K 8/368* (2013.01); *A61K 8/37* (2013.01); *A61L 9/012* (2013.01); *A61Q 15/00* (2013.01); *B32B 27/00* (2013.01); *C11D 3/2079* (2013.01); *C11D 3/2082* (2013.01); *C11D 3/3418* (2013.01); *D06N 7/0068* (2013.01); *D06N 7/0073* (2013.01); *A61L 2209/21* (2013.01); *C11D 3/0031* (2013.01)

(58) Field of Classification Search
CPC ........ A61L 9/01; A61L 9/012; A61L 2209/21; D06N 7/0068; D06N 7/0073; A61K 8/368; A61K 8/37; C11D 3/2079; C11D 3/2082; C11D 3/3418; C11D 3/0031; A61Q 15/00; B32B 27/00
See application file for complete search history.

(56) References Cited

U.S. PATENT DOCUMENTS

| | | |
|---|---|---|
| 3,953,450 A | 4/1976 | Bouillon et al. |
| 5,880,076 A | 3/1999 | Vermeer |
| 7,033,579 B1 | 4/2006 | Scavone |
| 7,901,619 B2 | 3/2011 | Mueller et al. |
| 2003/0008787 A1 | 1/2003 | McGee et al. |
| 2003/0118621 A1 | 6/2003 | Heidenfelder et al. |
| 2006/0165622 A1 | 7/2006 | Hiramoto et al. |
| 2008/0054089 A1 | 3/2008 | Oldfield et al. |
| 2008/0206093 A1 | 8/2008 | Muller et al. |
| 2008/0207774 A1 | 8/2008 | Krishnan |
| 2008/0233062 A1* | 9/2008 | Krishnan ............ A61K 31/7048 424/59 |
| 2009/0214457 A1 | 8/2009 | Dierker et al. |
| 2013/0085186 A1 | 4/2013 | Wendel et al. |
| 2013/0136713 A1 | 5/2013 | Terada et al. |
| 2014/0044761 A1 | 2/2014 | Lei et al. |
| 2014/0170102 A1 | 6/2014 | Cetti et al. |
| 2017/0087199 A1 | 3/2017 | Patron et al. |
| 2017/0335510 A1 | 11/2017 | Welch et al. |

FOREIGN PATENT DOCUMENTS

| | | | |
|---|---|---|---|
| CN | 1406574 A | 4/2003 | |
| CN | 102712882 A | 10/2012 | |
| CN | 104560398 A | 4/2015 | |
| EP | 0147759 A2 | 7/1985 | |
| EP | 1561476 A1 | 8/2005 | |
| JP | H06335614 A * | 12/1994 | ............ B01D 53/04 |
| JP | H08231315 A * | 9/1996 | ............ A01N 43/647 |
| JP | 2937337 B2 | 8/1999 | |
| JP | 2001-40316 A * | 2/2001 | ............ C09J 157/00 |
| JP | 2004167218 A | 6/2004 | |
| JP | 2011079750 A | 4/2011 | |
| JP | 2014-37660 A | 2/2014 | |
| KR | 1020080025054 A | 3/2008 | |
| KR | 1020140081874 A | 7/2014 | |
| RU | 2499607 C2 | 11/2013 | |
| WO | 02/069924 A1 | 9/2002 | |
| WO | 2006/103037 A2 | 10/2006 | |
| WO | 2008034764 A2 | 3/2008 | |
| WO | 2010019180 A1 | 5/2009 | |

(Continued)

OTHER PUBLICATIONS

English translation of JPH08231315A (Year: 1996).*
English translation of JP200140316A (Year: 2001).*
English translation of H06335614A (Year: 1994).*
International Preliminary Report on Patentability for PCT/US2018/055349 issued on Apr. 14, 2020, all enclosed pages cited.
International Search Report and Written Opinion of corresponding application PCT/US2018/055349, mailed Feb. 8, 2019, all enclosed pages cited.

(Continued)

*Primary Examiner* — Aradhana Sasan
(74) *Attorney, Agent, or Firm* — Shumaker, Loop & Kendrick, LLP

(57) ABSTRACT

A deodorant composition comprising a compound containing an aryl group and exhibiting an acidic property, a carrier, and an optional compatibilizing agent.

7 Claims, No Drawings

(56) References Cited

FOREIGN PATENT DOCUMENTS

| WO | 2010/079468 A2 | 7/2010 |
| WO | 2014/031353 A2 | 2/2014 |
| WO | 2015082380 A1 | 6/2015 |
| WO | 2016/061439 A1 | 4/2016 |
| WO | 2017/058594 A1 | 4/2017 |
| WO | 2017/133754 A1 | 8/2017 |

OTHER PUBLICATIONS

Supplementary European Search Report, EP 18866175, dated Jun. 8, 2021, 6 pages.
Extended European Search Report, EP 18866175, dated Oct. 19, 2021, 21 pages.
Shigabiyeva Y.A. Colloid-chemical properties of foaming and gel compositions with biologically active components: Ph. D. thesis in Chemistry, Kazan, 2014. 158 p., pp. 8, 10, 113, Chapter 1.3.
Russian Federation Search Report, in Appl No. 2020115457 in Russia, Issued Apr. 14, 2021 in Appl No. 2020115457 in Russia, (all enclosed pages cited).
Office Action in Chinese Patent Application No. 201880065893.4, Issued Jul. 22, 2022 (all enclosed pages cited).
Brazilian Office Action for BR Patent Application No. BR112020006383-5; dated Apr. 20, 2023 (5 Pages).
Mexican Office Action for MX Application No. MX/a/2020/003631; dated Jun. 1, 2023 (3 Pages).
Mexican Office Action for MX Application No. MX/a/2020/003631; dated Dec. 6, 2022 (2 Pages).
Korean Office Action for KR Application No. 10-2020-7010154 ; dated Jun. 27, 2023 (3 Pages).

* cited by examiner

ODOR CONTROL COMPOSITION AND CARPET HAVING A DURABLE ODOR CONTROL PROPERTY

CROSS-REFERENCE TO RELATED APPLICATIONS

This application claims priority from U.S. provisional patent application No. 62/570,786, filed on Oct. 11, 2017, in the United States Patent and Trademark Office. The disclosure of which is incorporated herein by reference in its entirety.

FIELD OF THE INVENTION

The present invention relates to a composition for odor control and to a carpet having a durable odor control property.

BACKGROUND OF THE INVENTION

Odor mitigation products for carpet are highly desirable. Current technologies are topically applied on fibers during manufacture or as an occasional freshening product by consumers. These products focus on the carpet fibers, which are usually washable and thus cleanable. However, malodors trapped in the carpet backing layer persist and continue to generate lingering odors. Environmental odors that are heavier than air (such as smoke, cooking odors) are the most noticeable ones. The majority of pet owners avoid carpet since it is almost impossible to get rid of the urine smell after their pets have accidents. There has been a limited focus on odor mitigation for carpet backing. Some products on the market claim to have deodorant properties once incorporated into a matrix but data demonstrates that this is not the case.

Present technologies work topically as an independent coating material or as a volatile molecule capture, thus do not work well when they are incorporated into a material. Some industry standard technologies that can be incorporated into the backing material, lose ability to control odors once incorporated.

Thus, there is a need for an odor control carpet having a durable odor control property.

SUMMARY OF THE INVENTION

The present invention relates to a durable composition for odor control and to a carpet having a durable odor control property.

In an embodiment of the invention, a deodorant composition comprising a compound containing an aryl group and exhibiting an acidic property, a carrier, and an optional compatibilizing agent is provided.

In an embodiment of the invention, a deodorant latex composition comprising a compound containing an aryl group and exhibiting an acidic property, a carrier, a latex, and an optional compatibilizing agent is provided.

In an embodiment of the invention, a method of making a deodorant latex composition comprising combining the deodorant composition with the latex is provided.

In an embodiment of the invention, a carpet comprising a deodorant latex composition having been applied to or incorporated into a backing material of the carpet is provided.

Further areas of applicability of the present invention will become apparent from the detailed description provided hereinafter. It should be understood that the detailed description and specific examples, while indicating the preferred embodiments of the invention, are intended for purposes of illustration only and are not intended to limit the scope of the invention.

DESCRIPTION OF THE PREFERRED EMBODIMENTS

The following description of the embodiments of the present invention is merely exemplary in nature and is in no way intended to limit the invention, its application, or uses. The present invention has broad potential application and utility. The following description is provided herein solely by way of example for purposes of providing an enabling disclosure of the invention, but does not limit the scope or substance of the invention.

In an embodiment of the invention, a deodorant composition having a durable odor control property is provided. The term "durable," as used herein means, that the property cannot be washed away or readily removed with normal use patterns or without a significant number of launderings. The deodorant composition comprises at least one compound containing an aryl group and exhibiting an acidic property. The deodorant composition further comprises a carrier such as water or an oil based carrier such as an organic ester or glycols, and an optional compatibilizing agent.

Categories of compounds containing an aryl group and exhibiting an acidic property include, but are not limited to: (1) aromatic species which contain as part of their structure a carboxylic acid (such as oleic acid, stearic acid, cinnamic acid, salicyclic acid), a polymeric acid (a polymer with acid groups such as a polyacrylic acid, polylactic acid), a sulfonic acid, or a phenolic group, and the anhydrides and the esters with Lewis acid behavior of these compounds; (2) naturally derived heterocycles such as purine- and pyrimidine based structures including uric acid; (3) derivatives of pyridine such as pyridine-2-thione N-oxide, and inorganic salts and complexes of substituted pyridines; (4) heterocycles such as furan, 4H-pyran, pyrrole, imidazole, pyrazole, triazole, pyrimidine, pyridazine, pyrazine, thiophene, oxazole, and thiazole, and derivatives of these compounds, and inorganic salts and complexes of substituted heterocycles.

As to category (1), examples of aromatic species which contain as part of their structure a carboxylic acid, a polymeric acid, sulfonic acid, or a phenolic group and the esters and anhydrides of these compounds, include, but are not limited to: (1) benzoic acid and related saturated or unsaturated acids in the homologous series such as 2-phenylacetic acid, cinnamic acid, phenylpropionic acid, and substituted forms of this group of acids, with substitutions to modify pKa, solubility, or hydrophobicity; (2) benzenesulfonic acid and substituted benzenesulfonic acids, with substitutions to modify pKa, solubility, or hydrophobicity; (3) phenylboronic acid and substituted phenylboronic acids, with substitutions to modify pKa, solubility, or hydrophobicity; (4) phenol and substituted phenols, with substitutions to modify pKa, solubility, or hydrophobicity; (5) phenylphosphonic acid and substituted phenylphosphonic acids, with substitutions to modify pKa, solubility, or hydrophobicity; (6) heterocyclic acids such as picolinic acid and nicotinic acid and substituted heterocyclic acids, with substitutions to modify pKa, solubility, or hydrophobicity; (7) phthalic acid and isomers of phthalic acid such as isophthalic acid and terephthalic acid, and substituted forms of phthalic acid and its isomers, with substitutions to modify pKa, solubility, or hydrophobicity; (8) naphthoic acid, isomers of naphthoic acid, and substituted naphthoic acids, with substitutions to modify pKa, solubility, or hydrophobicity; (9) naphthalenesulfonic acid, isomers of naphthalenesulfonic acid, and substituted naphthalenesulfonic acids, with substitutions to modify pKa, solubility, or hydrophobicity; (10) polystyrene carboxylates or sulfonates, or copolymers containing these groups. Such substitutions are readily known to one of ordinary skill in the art without undue experimentation.

Gallic acid and its derivatives are non-limiting examples of a substituted benzoic acid or phenol under categories (1) and (4). Sulfobenzoic acid and its derivatives are non-limiting examples under category (2). Sulfophathalic acid and its derivatives are non-limiting examples under category (7). Phosphonic acid and its derivatives are non-limiting examples under category (5). The derivatives are included in each category as "substitutions."

A compatibilizing agent is a chemical used to prevent the interaction of the deodorant compound with the latex. Whether or not a compatibilizing agent is used may depend upon the latex formulation. If the latex has pH<7, a compatibilizing agent is not typically needed. If the latex pH>7, a compatibilizing agent is typically needed. With "acids" that are either not water soluble or low water soluble, the low water solubility leads to low dissociation rate when introducing to the water-based latex, thus reduce the effect of the "acid" on the system pH. With "acids" that are more water soluble, high dissociation rate at the latex system pH, which can cause significant changes in pH of the latex.

There are several non-limiting examples of compatibilizing agents and methods for compatibilizing including, but not limited to, use of a buffering agent such as monopotassium phosphate or N-Cyclohexyl-2-aminoethanesulfonic acid, use of a conjugate base of carboxylic, sulfonic or other organic acids such as sodium lauryl sulfate and/or organic esters of such acids, and encapsulation of the "acid" in a polymeric shell, among others.

Other additives may be present in the deodorant composition including, but not limited to, a dispersing agent such as a hydrocolloid, a thickening agent such as fumed silica, polyacrylate, and polyethylacrylate.

The deodorant composition may be in a powder form or in a liquid form. However, a liquid delivery system may be preferred to achieve a good mixing between latex and the deodorant composition.

In an embodiment of the invention, the deodorant composition is combined or mixed with a latex to form a deodorant latex composition. A latex is a dispersion of polymer particles in water. Fillers, surfactants, thickeners, pigments, stabilizers and other additives are other possible ingredients in the latex, depending on the final usage. The deodorant composition is compatible with various aqueous based latexes and can be used in any application where latex is used.

In an embodiment of the invention, the deodorant latex composition is incorporated into a backing material of a carpet, preferably during the manufacturing process for the carpet.

The deodorant composition of the present invention can be used as an add-on additive in multiple aqueous based formulations. Thus, the deodorant composition does not require a separate process or to alter the articles' surface properties. In addition, latex provides a medium in which the aromatic groups can be oriented, creating a surface for molecular interaction and odor capture of aromatics, nonpolar, and basic molecules. Since materials like latex absorb odors, this deodorant composition provides a solution that is built-in to the latex material, more efficient, better than current technologies in terms of its odor adsorption capacity and the range of chemical classes of odorants the deodorant composition can adsorb.

In an embodiment of the invention, a method of making a deodorant composition is provided. The method comprises combining a compound containing an aryl group and exhibiting an acidic property, an optional compatibilizing agent, and a carrier such as water.

In an embodiment of the invention, a method of making a deodorant latex composition is provided. The method comprises combining or mixing the deodorant composition with a latex to form a deodorant latex composition.

In an embodiment of the invention, a method of using the deodorant latex composition is provided. The method comprises applying the deodorant latex composition to a backing material of a carpet as secondary backing.

In an embodiment of the invention, a carpet having the deodorant composition therein is provided.

EXAMPLES

Example Formulation 1

TABLE 1

| Material | % (by weight) |
|---|---|
| Terephthalic acid | 50 |
| Hydrocolloid | 0.5 |
| Water | 49.5 |

Example Formulation 2

TABLE 2

| Material | % (by weight) |
|---|---|
| Terephthalic acid | 25 |
| Benzoic acid | 25 |
| Hydrocolloid | 0.5 |
| Water | 24.75 |
| Ethylene glycol | 24.75 |

Example Formulation 3

TABLE 3

| Material | % (by weight) |
|---|---|
| Bis(2-ethylhexyl) terephthalate | 94.95 |
| Terephthalic acid | 5 |
| Fumed silica | 0.05 |

Example Formulation 4

TABLE 4

| Material | % (by weight) |
|---|---|
| Terephthalic acid encapsulated in melamine formaldehyde shell | 32 |
| Water | 68 |

The deodorant composition can be incorporated into latex material as well as most aqueous based formulas to render odor mitigation performance to the final articles. Latex is a popular material for carpet, rug, liner backing as well as binders and paints.

Experimental tests were conducted using the deodorant latex formulation for carpet backing. These were compared to multiple industry standard deodorant packages such as zeolites. Each of the deodorant formulations above were added to latex at different levels as indicated in Table 1. The treated and untreated latexes were cured overnight at 40° C. and then placed in sealed vials. Odorants (pyridine, nonenal and triethylamine) were introduced to the samples. After 2 hours, headspace vapors were analyzed by gas chromatography to determine the amount of odorants in the headspace. Reductions were calculated against the untreated latex.

Pyridine is a heterocyclic organic compound harmful to human with an unpleasant odor that often comes from cigarette smoke and (burn) cooking activities. Nonenal is an unsaturated aldehyde which odor has been associated with aged human body odor. Triethylamine (TEA) has a strong fishy odor and was used as representative for a class of odor that contains amine groups.

TABLE 5

|  | Use rate | % reduction | | |
|---|---|---|---|---|
|  |  | Pyridine | Nonenal | TEA |
| Commercially available deodorant | 4.2 wt. % | 56 | 79 | 100 |
| Commercially available deodorant | 1.5 wt. % | 35 | NR | 29 |
| Formulation 1 | 2.0 wt. % | 75 | 83 | 100 |
| Formulation 1 | 1.0 wt. % | 76 | 80 | 100 |
| Formulation 2 | 2.0 wt. % | 83 | 85 | 100 |
| Formulation 3 | 1.5 wt. % | 33 | 65 | 65 |
| Formulation 4 | 1.5 wt. % | 70 | 48 | 100 |

It was surprisingly found that the compositions presented here outperform industry standard technologies in head to head comparisons demonstrating a unique and durable odor control ability to these components.

It will therefore be readily understood by those persons skilled in the art that the present invention is susceptible of broad utility and application. Many embodiments and adaptations of the present invention other than those herein described, as well as many variations, modifications and equivalent arrangements, will be apparent from or reasonably suggested by the present invention and the foregoing description thereof, without departing from the substance or scope of the present invention. Accordingly, while the present invention has been described herein in detail in relation to its preferred embodiment, it is to be understood that this disclosure is only illustrative and exemplary of the present invention and is made merely for purposes of providing a full and enabling disclosure of the invention. The foregoing disclosure is not intended or to be construed to limit the present invention or otherwise to exclude any such other embodiments, adaptations, variations, modifications and equivalent arrangements.

What is claimed is:

1. A latex deodorant composition comprising:
   latex; and
   a deodorant composition, the deodorant composition comprising:
      from 50 weight percent to 99.95 weight percent of a compound containing an aryl group and exhibiting an acidic property selected from the group consisting of: terephthalic acid, benzoic acid, phenylacetic acid, phenylpropionic acid, phenylboronic acid, picolinic acid, nicotinic acid, phthalic acid, isophthalic acid, naphthoic acid, naphthalenesulfonic acid, gallic acid, sulfobenzoic acid, sulfophthalic acid, phenylphosphonic acid, bis(2-ethylhexyl) terephthalate, and combinations thereof,
      a carrier, and
      a compatibilizing agent;
   wherein the latex deodorant composition has a durable odor control.

2. The latex deodorant composition according to claim 1, wherein the latex deodorant composition reduces triethylamine odors by 65% to 100%.

3. The latex deodorant composition according to claim 1, wherein the latex deodorant composition reduces pyridine odors by 33% to 83%.

4. The latex deodorant composition according to claim 1, wherein the latex deodorant composition reduces nonenal odors by 48% to 85%.

5. The latex deodorant composition according to claim 1, wherein the latex deodorant composition comprises from 1 weight percent to 2 weight percent of the deodorant composition.

6. The latex deodorant composition according to claim 5, wherein the latex deodorant composition comprises at least 98 weight percent latex.

7. A latex deodorant composition, consisting of:
   latex; and
   a deodorant composition, the deodorant composition comprising:
      from 25 weight percent to 99.95 weight percent of a compound containing an aryl group and exhibiting an acidic property selected from the group consisting of: terephthalic acid, benzoic acid, phenylacetic acid, phenylpropionic acid, phenylboronic acid, picolinic acid, nicotinic acid, phthalic acid, isophthalic acid, naphthoic acid, naphthalenesulfonic acid, gallic acid, sulfobenzoic acid, sulfophthalic acid, phenylphosphonic acid, bis(2-ethylhexyl) terephthalate, and combinations thereof,
      a carrier, and
      a compatibilizing agent;
   wherein the latex deodorant composition has a durable odor control.

\* \* \* \* \*